United States Patent [19]

Wollweber et al.

[11] Patent Number: 4,871,761

[45] Date of Patent: Oct. 3, 1989

[54] SUBSTITUTED PROPYLAMINE PESTICIDES

[75] Inventors: Detlef Wollweber, Wuppertal; Stefan Dutzmann, Duesseldorf, both of Fed. Rep. of Germany

[73] Assignee: Bayer Aktiengesellschaft, Leverkusen, Fed. Rep. of Germany

[21] Appl. No.: 170,522

[22] Filed: Mar. 18, 1988

[30] Foreign Application Priority Data

Apr. 3, 1987 [DE] Fed. Rep. of Germany ....... 3711345

[51] Int. Cl.$^4$ ..................... A01N 43/16; A01N 43/08; C07D 309/04; C07D 307/14
[52] U.S. Cl. .................................. 514/438; 549/414; 549/426; 549/472; 549/492; 549/59; 549/60; 549/74; 549/75; 549/417; 549/419; 549/473; 549/475; 549/476; 549/478; 549/479; 549/484; 549/494; 549/495; 549/62; 549/65; 549/72; 514/444; 514/445; 514/459; 514/471
[58] Field of Search ............... 549/414, 426, 472, 492, 549/59, 60, 74, 75, 417, 419, 473, 475, 476, 478, 479, 484, 494, 495, 62, 65, 72; 514/459, 471, 438, 444, 445

[56] References Cited

FOREIGN PATENT DOCUMENTS 0158922 10/1985 European Pat. Off. .
0224163 6/1987 European Pat. Off. .
2656747 6/1978 Fed. Rep. of Germany .
2825961 1/1980 Fed. Rep. of Germany .
3541181 5/1987 Fed. Rep. of Germany .

OTHER PUBLICATIONS

Patent Abstracts of Japan–vol. 9, No. 145 (C–287) (1868)–Jun. 20, 1985.

*Primary Examiner*—Nicky Chan
*Attorney, Agent, or Firm*—Sprung, Horn Kramer & Woods

[57] ABSTRACT

Novel pesticides of the formula

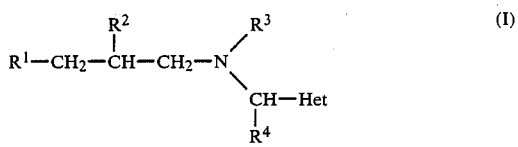

in which

R$^1$ represents in each case optionally substituted cycloalkyl, cycloalkenyl, tetrahydronaphthyl, decahydronaphthyl, phenyl, naphthyl or thienyl, R$^2$ represents alkyl, R$^3$ represents hydrogen alkyl, alkenyl, alkinyl, hydroxyalkyl, alkoxyalkyl, dialkoxyalkyl, hydroxyalkoxyalkyl, cyano or formyl, or in each case optionally substituted cycloaklyl, cycloalkenyl, cycloalkylalkyl, cycloalkenylalkyl, aralkyl, aryl, furanylmethyl or tetrahydrofuranylmethyl, R$^4$ represents hydrogen or alkyl, and Het represents an optionally substituted heterocyclic ring of the formula

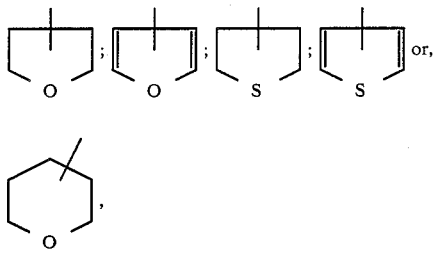

and acid-addition salts thereof.

10 Claims, No Drawings

SUBSTITUTED PROPYLAMINE PESTICIDES

The invention relates to new substituted propylamines, several processes for their preparation, and their use as pesticides.

It has already been disclosed that certain substituted propylamines, such as, for example, 1-(4-t-butylphenyl)-2-methyl-3-(2,6-dimethylmorpholin-4-yl)-propane, have fungicidal properties (cf. DE-OS (German Published Specification) 2,656,747).

However, the action of these previously known compounds is not completely satisfactory in all areas of application, in particular at low application rates and concentrations.

New substituted propylamines of the general formula (I)

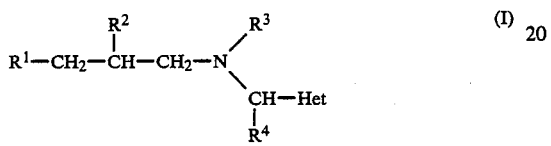

in which
- $R^1$ represents in each case optionally substituted cycloalkyl, cycloalkenyl, tetrahydronaphthyl, decahydronaphthyl, phenyl, naphthyl or thienyl,
- $R^2$ represents alkyl,
- $R^3$ represents hydrogen, alkyl, alkenyl, alkinyl, hydroxyalkyl, alkoxyalkyl, dialkoxyalkyl, hydroxyalkoxyalkyl, cyano or formyl, or in each case optionally substituted cycloalkyl, cycloalkenyl, cycloalkylalkyl, cycloalkenylalkyl, aralkyl, aryl, furanylmethyl or tetrahydrofuranylmethyl,
- $R^4$ represents hydrogen or alkyl, and
- Het represents an optionally substituted heterocyclic ring of the formula

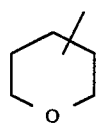

and the plant-tolerated acid-addition salts thereof, have been found.

It has furthermore been found that the new substituted propylamines of the general formula (I)

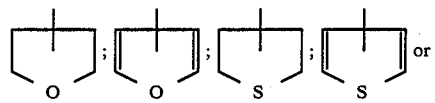

in which
- $R^1$ represents in each case optionally substituted cycloalkyl, cycloalkenyl, tetrahydronaphthyl, decahydronaphthyl, phenyl, naphthyl or thienyl,
- $R^2$ represents alkyl,
- $R^3$ represents hydrogen, alkyl, alkenyl, alkinyl, hydroxyalkyl, alkoxyalkyl, dialkoxyalkyl, hydroxyalkoxyalkyl, cyano or formyl, or in each case optionally substituted cycloalkyl, cycloalkenyl, cycloalkylalkyl, cycloalkenylalkyl, aralkyl, aryl, furanylmethyl or tetrahydrofuranylmethyl,
- $R^4$ represents hydrogen or alkyl, and
- Het represents an optionally substituted heterocyclic ring of the formula

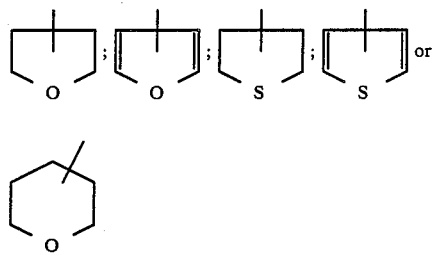

and the plant-tolerated acid-addition salts thereof, are obtained when
(a) substituted aldehydes of the formula (II)

in which
$R^1$ and $R^2$ have the abovementioned meaning, are reacted with amines of the formula (III)

in which
$R^3$, $R^4$ and Het have the abovementioned meaning, in the presence of a reducing agent and if appropriate in the presence of a diluent and if appropriate in the presence of a catalyst, or when
(b) the substituted propylamines of the formula (Ia)

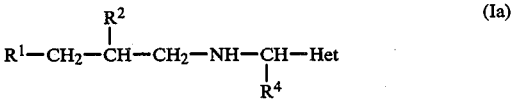

in which
$R^1$, $R^2$, $R^4$ and Het have the abovementioned meaning, which are obtainable with the aid of process (a) according to the invention are reacted with alkylating agents of the formula (IV)

$$R^{3-1}-E \qquad (IV)$$

in which
$R^{3-1}$ represent alkyl, alkenyl, alkinyl, hydroxyalkyl, alkoxyalkyl, dialkoxyalkyl, hydroxyalkoxyalkyl or in each case optionally substituted cycloalkyl, cycloalkenyl, cycloalkylalkyl, cycloalkenylalkyl, aralkyl, furanylmethyl or tetrahydrofuranylmethyl, and E represents an electron-withdrawing leaving group, if appropriate in the presence of a diluent and if appropriate in the presence of a reaction auxiliary, or when (c) the substituted propylamines of the formula (Ib)

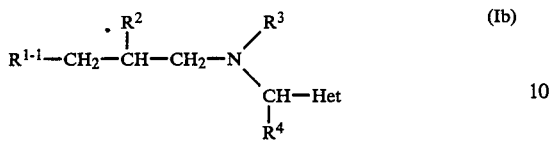

in which

R$^{1-1}$ represents in each case optionally substituted phenyl or naphthyl, and R$^2$, R$^3$, R$^4$ and Het have the abovementioned meaning, which are obtainable with the aid of process (a) or (b) according to the invention, are hydrogenated using hydrogen in the presence of a catalyst and if appropriate in the presence of a diluent, and, if appropriate, an acid is subsequently adducted.

Finally, it has been found that the new substituted propylamines of the general formula (I) have a good action against pests, in particular against fungal pests.

Surprisingly, the substituted propylamines of the general formula (I) according to the invention exhibit a considerably better fungicidal activity than the substituted propylamines which are known from the prior art, such as, for example, 1-(4-t-butylphenyl)-2-methyl-3-(2,6-dimethylmorpholin-4-yl)-propane, which are similar compounds chemically and regarding their action.

Formula (I) provides a general definition of the substituted propylamines according to the invention. Preferred compounds of the formula (I) are those in which R$^1$ represents in each optionally monosubstituted to polysubstituted cycloalkyl or cycloalkenyl in each case having 3 to 10 carbon atoms, the substituents being identical or different and suitable substituents being: straight-chain or branched alkyl having 1 to 8 carbon atoms or cycloalkylalkyl having 1 to 8 carbon atoms in the straight-chain or branched alkyl part and 3 to 7 carbon atoms in the cycloalkyl part; in addition it represents in each case optionally monosubstituted to polysubstituted tetrahydronaphthyl or decahydronaphthyl, the substituents being identical or different and suitable substituents being: in each case straight-chain or branched alkyl or alkoxy in each case having 1 to 8 carbon atoms; in addition represents in each case monosubstituted to polysubstituted phenyl or naphthyl, the substituents being identical or different and suitable substituents being in each case: halogen, straight-chain or branched alkyl having 1 to 8 carbon atoms, in each case straight-chain or branched alkoxy or alkylthio in each case having 1 to 4 carbon atoms, in each case straight-chain or branched halogenoalkyl, halogenoalkoxy or halogenoalkylthio in each case having 1 to 4 carbon atoms and 1 to 9 identical or different halogen atoms, cycloalkyl having 3 to 7 carbon atoms, aryl or aryloxy having 6 to 10 carbon atoms which is in each case optionally monosubstituted to polysubstituted by identical or different, straight-chain or branched alkyl having 1 to 6 carbon atoms, and arylalkyl having 6 to 10 carbon atoms in the aryl part and 1 to 6 carbon atoms in the straight-chain or branched alkyl part; and finally represents optionally monosubstituted to polysubstituted thienyl, the substituents being identical or different and suitable substituents being: halogen, in each case straight-chain or branched alkyl or halogenoalkyl in each case having 1 to 8 carbon atoms and, if appropriate, 1 to 9 identical or different halogen atoms;

R$^2$ represents straight-chain or branched alkyl having 1 to 4 carbon atoms,

R$^3$ represents hydrogen, straight-chain or branched alkyl having 1 to 8 carbon atoms, in each case straight-chain or branched alkenyl or alkinyl in each case having 3 to 8 carbon atoms, in each case straight-chain or branched alkoxyalkyl, hydroxyalkoxyalkyl or dialkoxyalkyl in each case having 1 to 4 carbon atoms in the individual alkyl parts, straight-chain or branched hydroxyalkyl having 2 to 8 carbon atoms, cyano, formyl, cycloalkyl having 3 to 7 carbon atoms, cycloalkenyl having 3 to 7 carbon atoms, cycloalkylalkyl having 3 to 7 carbon atoms in the cycloalkyl part and 1 to 8 carbon atoms in the straight-chain or branched alkyl part, cycloalkenylalkyl having 3 to 7 carbon atoms in the cycloalkenyl part and 1 to 8 carbon atoms in the straight-chain or branched alkyl part, furanylmethyl or tetrahydrofuranylmethyl which is in each case optionally monosubstituted to polysubstituted by identical or different straight-chain or branched alkyl having 1 to 4 carbon atoms, or represents phenylalkyl having 1 to 4 carbon atoms in the straight-chain or branched alkyl part or phenyl which is in each case optionally monosubstituted to polysubstituted by identical or different substituents, suitable phenyl substituents being in each case: halogen, in each straight-chain or branched alkyl, alkoxy or alkylthio in each case having 1 to 4 carbon atoms, and in each case straight-chain or branched halogenoalkyl, halogenoalkoxy or halogenoalkylthio in each case having 1 to 4 carbon atoms and 1 to 9 identical or different halogens, R$^4$ represents hydrogen or straight-chain or branched alkyl having 1 to 4 carbon atoms, and Het represents an in each case monosubstituted to polysubstituted heterocyclic ring of the formula

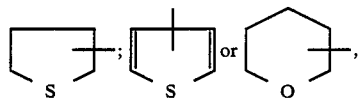

the substituents being identical or different and suitable substituents being in each case: in each case straight-chain or branched alkyl, alkoxy, alkylthio or alkoxycarbonyl in each case having 1 to 4 carbon atoms in the individual alkyl parts, and in each case straight-chain or branched halogenoalkyl, halogenoalkoxy or halogenoalkylthio in each case having 1 to 4 carbon atoms and 1 to 9 identical or different halogen atoms.

Particularly preferred compounds of the formula (I) according to the invention are those in which R¹ represents in each case optionally monosubstituted, disubstituted or trisubstituted cyclohexyl or cyclohexenyl, the substituents being identical or different and suitable substituents being in each case: methyl, ethyl, n- or i-propyl, n-, i-, s- or t-butyl, straight-chain or branched pentyl, straight-chain or branched hexyl, cyclohexylmethyl, 1-cyclohexylethyl, 1-cyclohexylpropyl, 1-cyclohexylbutyl, 2-cyclohexyl-2-propyl and 2-cyclohexyl-2-butyl; in addition represents optionally monosubstituted, disubstituted or trisubstituted tetrahydronaphthyl or decahydronaphthyl, the substituents being identical or different and suitable substituents being in each case: methyl, ethyl, n- or i-propyl, n-, i-, s- or t-butyl, straight-chain or branched pentyl, methoxy, ethoxy, n- or i-propoxy; in addition represents in each case optionally monosubstituted, disubstituted or trisubstituted phenyl or naphthyl, the substituents being identical or different and suitable substituents being in each case: fluorine, chlorine, bromine, methyl, ethyl, n- or i-propyl, n-, i-, s- or t-butyl, in each case straight-chain or branched pentyl, hexyl, heptyl or octyl, methoxy, ethoxy, n- or i-propoxy, n-, i-, s- or t-butoxy, methylthio, ethylthio, n- or i-propylthio, trifluoromethyl, trifluoromethoxy, trifluoromethylthio, cyclohexyl, phenyl, phenoxy, benzyl, 1-phenylethyl, 1-phenylpropyl, 2-phenyl-2-propyl and 2-phenyl-2-butyl, and finally represents 2-thienyl or 3-thienyl which is in each case optionally monosubstituted, disubstituted or trisubstituted by fluorine, chlorine, bromine, methyl, ethyl, n-or i-propyl, n- or i-, s- or t-butyl or trifluoromethyl, the substituents being identical or different;

R² represents methyl, ethyl, n- or i-propyl,

R³ represents hydrogen, methyl, ethyl, n- or i-propyl, n-, i-, s- or t-butyl, in each case straight-chain or branched pentyl, hexyl, heptyl or octyl, represent allyl, butenyl, propargyl, butinyl, methoxyethyl, methoxypropyl, ethoxyethyl, ethoxypropyl, propoxypropyl, dimethoxyethyl, hydroxyethyl, hydroxypropyl, hydroxyethoxyethyl, in each case optionally monosubstituted, disubstituted or trisubstituted cyclohexyl, cyclohexenyl, cyclopentyl, cyclohexylmethyl, cyclohexylethyl, cyclohexenylmethyl, cyclopentylmethyl, furanylmethyl or tetrahydrofuranylmethyl, the substituents being identical or different and suitable substituents being in each case: methyl, ethyl, n- or i-propyl, n-, i-, s- or t-butyl, and in addition represent in each case optionally monosubstituted, disubstituted or trisubstituted benzyl, phenylethyl or phenyl, the substituents being identical or different and suitable phenyl substituents being in each case: fluorine, chlorine, bromine, methyl, ethyl, n- or i-propyl, methoxy, ethoxy, methylthio, trifluoromethyl, trifluoromethoxy or trifluoromethylthio, R⁴ represents hydrogen, methyl, ethyl, n- or i-propyl, and Het represents an in each case optionally monosubstituted, disubstituted or trisubstituted heterocyclic ring of the formula

-continued

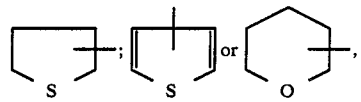

the substituents being identical or different and suitable substituents being: methyl, ethyl, n-or i-propyl, n-, i-, s- or t-butyl, methoxy, ethoxy, n- or i-propoxy or methylthio.

Preferred compounds according to the invention also include addition products of acids and substituted propylamines of the formula (I) in which the substituents R¹, R², R³, R⁴ and Het have the meaning which has already preferably been mentioned for these substituents.

The acids which can be added preferably include hydrohalic acids, such as, for example, hydrochloric acid and hydrobromic acid, in particular hydrochloric acid, furthermore phosphoric acid, nitric acid, mono, bi and trifunctional carboxylic acids and hydroxycarboxylic acids, such as, for example, formic acid, acetic acid, maleic acid, succinic acid, fumaric acid, tartaric acid citric acid, salicylic acid, sorbic acid and lactic acid furthermore sulphonic acids, such as p-toluenesulphonic acid and 1,5-naphthalenedisulphonic acid and saccharin.

Very particularly preferred compounds of the formula (I) according to the invention are those in which R¹ represents in each case optionally monosubstituted or disubstituted cyclohexyl or cyclohexenyl, the substituents being identical or different and suitable substituents being: i-propyl, t-butyl, neo-pentyl, 1,1-dimethylpropyl, 1,1,2-trimethylpropyl, cyclohexylmethyl or 2-cyclohexyl-2-propyl; in addition represents decahydronaphthyl which is optionally monosubstituted or disubstituted by methyl, ethyl, methoxy or ethoxy, the substituents being identical or different; furthermore represents in each case optionally monosubstituted or disubstituted phenyl or naphthyl, the substituents being identical or different particularly preferred phenyl substituents being: fluorine, chlorine, bromine, isopropyl, t-butyl, neo-pentyl, 1,1-dimethylpropyl, 1,1,2-trimethylpropyl, trifluoromethyl, trifluoromethoxy, cyclohexylmethyl, cyclohexyl, phenyl, phenoxy, benzyl, 1-phenylethyl or 2-phenyl-2-propyl, and particularly preferred naphthyl substituents being: methyl, ethyl, methoxy or ethoxy, and finally represents 2-thienyl or 3-thienyl which is in each case optionally substituted by chlorine, methyl, i-propyl or t-butyl, R² represents methyl, R³ represents hydrogen, methyl, ethyl, n- or i-propyl, n-, i- or s-butyl, n-pentyl, n-hexyl, n-octyl, allyl, propargyl, methxoyethyl, methoxypropyl, ethoxyethyl or ethoxypropyl, R⁴ represents hydrogen or methyl, and Het represents an optionally methyl-substituted heterocyclic ring of the formula

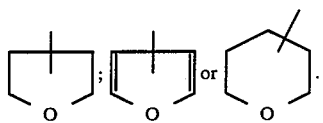

Halogen also represents fluorine, chlorine, bromine and iodine, in particular fluorine, chlorine and bromine, in the radicals such as halogenoalkyl, unless otherwise stated elsewhere. Preferred compounds are also those in which Het in the formula (I) are linked in the 2- or 3-position.

In addition, acid-addition compounds produced from compounds of the formula (I) with hydrogen chloride, formic acid, acetic acid, methanesulphonic acid, p-toluenesulphonic acid, 1,6-naphthalenedisulphonic acid and saccharin are particularly preferred.

The following substituted propylamines of the general formula (I) may be mentioned individually, in addition to the compounds mentioned in the preparation examples:

$$R^1-CH_2-CH(R^2)-CH_2-N(R^3)(CH(R^4)-Het) \quad (I)$$

| $R^1$ | $R^2$ | $R^3$ | $R^4$ | Het |
|---|---|---|---|---|
| (CH₃)₃C—[cyclohexyl-H]— | CH₃ | —(CH₂)₂—CH₃ | H | [2,5-dihydrofuran] |
| (CH₃)₃C—[cyclohexyl-H]— | CH₃ | —(CH₂)₂—CH₃ | H | [tetrahydropyran] |
| (CH₃)₃C—[cyclohexyl-H]— | CH₃ | —(CH₂)₂—CH₃ | H | [tetrahydrofuran] |
| (CH₃)₃C—[cyclohexyl-H]— | CH₃ | —(CH₂)₂—CH₃ | H | [2,5-dihydrofuran] |
| (CH₃)₃C—[phenyl]— | CH₃ | —(CH₂)₂—CH₃ | H | [tetrahydrofuran] |
| (CH₃)₃C—[cyclohexyl-H]— | CH₃ | —(CH₂)₂—CH₃ | H | [tetrahydropyran] |
| [cyclohexyl-H]—[phenyl]— | CH₃ | —CH₂—CH(CH₃)₂ | H | [2,5-dihydrofuran] |
| (CH₃)₃C—[phenyl]— | CH₃ | —(CH₂)₂—CH₃ | H | [2-methyltetrahydrofuran] |
| C₂H₅—C(CH₃)₂—[phenyl]— | CH₃ | —(CH₂)₂—CH₃ | H | [tetrahydrofuran] |
| (CH₃)₃C—[phenyl]— | CH₃ | —(CH₂)₂—CH₃ | CH₃ | [tetrahydrofuran] |

-continued
$$R^1-CH_2-\underset{R^2}{\overset{}{C}H}-CH_2-\underset{\underset{R^4}{\overset{}{C}H-Het}}{\overset{R^3}{N}}$$ (I)
| $R^1$ | $R^2$ | $R^3$ | $R^4$ | Het |
|---|---|---|---|---|
| 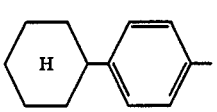 | $CH_3$ | $-(CH_2)_2-CH_3$ | $CH_3$ | 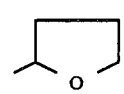 |
| 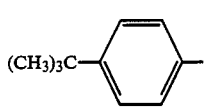 | $-CH(CH_3)_2$ | 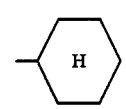 | $C_2H_5$ | 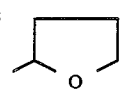 |
| 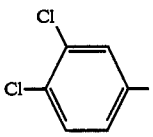 | $-(CH_2)_3-CH_3$ | $C_2H_5$ | $CH_3$ | 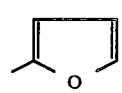 |
| 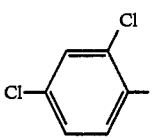 | $C_2H_5$ | $C_2H_5$ | $C_2H_5$ | 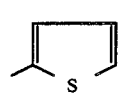 |
| 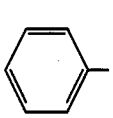 | $CH_3$ | $-(CH_2)_2-CH_3$ | H | 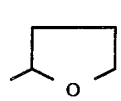 |
| 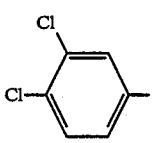 | $CH_3$ | $-(CH_2)_2-CH_3$ | H | 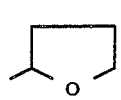 |
| 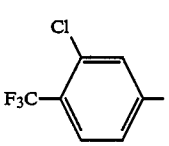 | $CH_3$ | $-(CH_2)_2-CH_3$ | H | 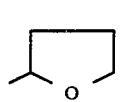 |
| 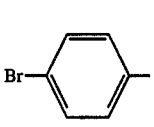 | $CH_3$ | $-(CH_2)_2-CH_3$ | H | 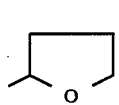 |
| 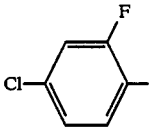 | $CH_3$ | $-(CH_2)_2-CH_3$ | H | 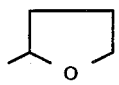 |
| 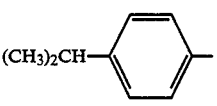 | $CH_3$ | $-(CH_2)_2-CH_3$ | H | 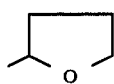 |
| 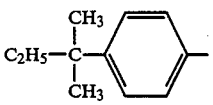 | $CH_3$ | $-(CH_2)_2-CH_3$ | H | 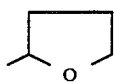 |

$$R^1-CH_2-\underset{R^2}{\overset{}{CH}}-CH_2-\underset{\underset{R^4}{\overset{}{CH-Het}}}{\overset{R^3}{N}}$$ (I)
| R¹ | R² | R³ | R⁴ | Het |
|---|---|---|---|---|
| 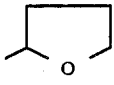 | CH₃ | —(CH₂)₂—CH₃ | H | 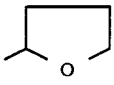 |
| 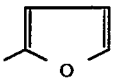 | CH₃ | —(CH₂)₂—CH₃ | H | 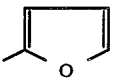 |
| 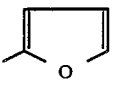 | CH₃ | H | H | 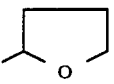 |
| 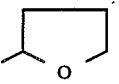 | CH₃ | H | H | 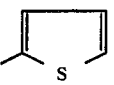 |
| 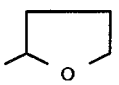 | CH₃ | CH₃ | H | 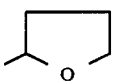 |
| 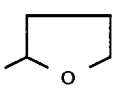 | CH₃ | C₂H₅ | H | 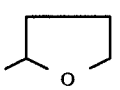 |
| (CH₃)₃C—⌬— | CH₃ | —(CH₂)₃—CH₃ | H | ⌬O |
| (CH₃)₃C—⌬— | CH₃ | —CH(CH₃)₂ | H | ⌬S |
| (CH₃)₃C—⌬— | CH₃ | —CH(CH₃)—(CH₂)₂—CH₃ | H | ⌬O |
| (CH₃)₂CH—C(CH₃)₂—⌬— | CH₃ | —CH₂—CH(CH₃)₂ | H | ⌬O |
| (CH₃)₃C—⌬— | CH₃ | —C(CH₃)₃ | H | ⌬O |
| (CH₃)₃C—⌬— | CH₃ | —(CH₂)₇—CH₃ | H | ⌬O |

-continued
$$R^1-CH_2-\underset{R^2}{\underset{|}{CH}}-CH_2-\underset{\underset{R^4}{|}}{\overset{\overset{R^3}{|}}{N}}-Het \qquad (I)$$
| R¹ | R² | R³ | R⁴ | Het |
|---|---|---|---|---|
| 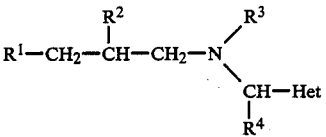 | CH₃ | 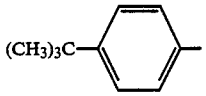 | H | 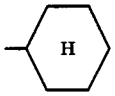 |
| 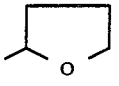 | CH₃ | 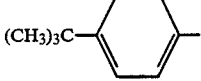 | H | 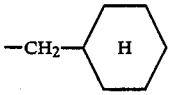 |
| 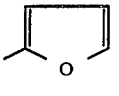 | CH₃ | 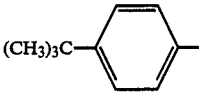 | H | 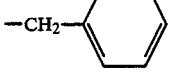 |
| 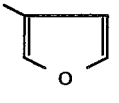 | CH₃ | 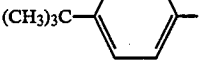 | H | 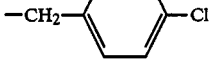 |
| 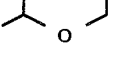 | CH₃ | 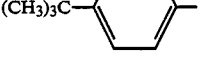 | H | 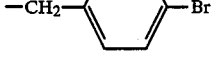 |
| 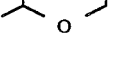 | CH₃ | 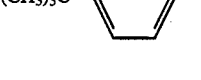 | H | 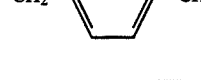 |
| 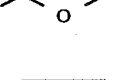 | CH₃ | —CH₂—CH₂— 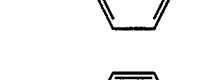 | H |  |
| 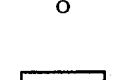 | CH₃ | 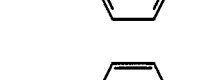 | H | 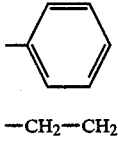 |
| 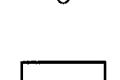 | CH₃ | —CH₂—CH₂—OCH₃ | H | 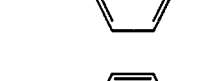 |
| 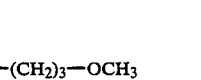 | CH₃ | —(CH₂)₃—OCH₃ | H | 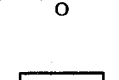 |
| 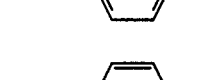 | CH₃ | —(CH₂)₃—OC₂H₅ | H | 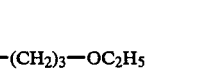 |
| 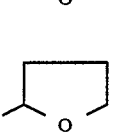 | CH₃ |  | H |  |

-continued $$R^1-CH_2-CH(R^2)-CH_2-N(R^3)(CH(R^4)-Het) \quad (I)$$

| R¹ | R² | R³ | R⁴ | Het |
|---|---|---|---|---|
| (CH₃)₃C-C₆H₄- | CH₃ | -C(=O)-H | H | 2-tetrahydrofuryl |
| (CH₃)₃C-C₆H₄- | CH₃ | -CN | H | 2-tetrahydrofuryl |
| C₂H₅(CH₃)₂C-C₆H₄- | CH₃ | C₂H₅ | H | 2-tetrahydrofuryl |
| (CH₃)₃C-C₆H₄- | CH₃ | CH₃ | H | 2,5-dimethylthiophen-3-yl |
| biphenyl-4-yl | CH₃ | -(CH₂)₃-CH₃ | C₂H₅ | 2-furyl |
| 2,4,5-trichlorophenyl | CH₃ | cyclohexyl | H | 2-tetrahydrofuryl |
| (CH₃)₃C-C₆H₄- | CH₃ | -CH₂-CH=CH₂ | H | 2-tetrahydrofuryl |
| (CH₃)₃C-C₆H₄- | CH₃ | -CH₂-C≡CH | H | 2-tetrahydrofuryl |
| 2-naphthyl | CH₃ | -(CH₂)₂-CH₃ | H | 2-tetrahydrofuryl |
| decahydronaphth-2-yl | CH₃ | -(CH₂)₂-CH₃ | H | 2-tetrahydrofuryl |
| 4-(2-phenylpropan-2-yl)phenyl | CH₃ | -(CH₂)₂-CH₃ | H | 2-tetrahydrofuryl |

-continued $$R^1-CH_2-\underset{R^2}{CH}-CH_2-\underset{\underset{R^4}{|}}{\underset{|}{N}}\underset{CH-Het}{\overset{R^3}{\diagup}} \quad (I)$$

| R¹ | R² | R³ | R⁴ | Het |
|---|---|---|---|---|
| 4-(tert-butyl)cyclohex-3-en-1-yl | CH₃ | —(CH₂)₂—CH₃ | H | tetrahydrofuran-2-yl |
| 3-(tert-butyl)cyclohex-2-en-1-yl | CH₃ | —(CH₂)₂—CH₃ | H | tetrahydrofuran-2-yl |
| thiophen-2-yl | CH₃ | —(CH₂)₂—CH₃ | H | tetrahydrofuran-2-yl |
| 5-(tert-butyl)thiophen-2-yl | CH₃ | —(CH₂)₂—CH₃ | H | tetrahydrofuran-2-yl |
| biphenyl-4-yl | CH₃ | —(CH₂)₂—CH₃ | H | tetrahydrofuran-2-yl |
| 4-(tert-butyl)cyclohexyl | CH₃ | —CH₂—CH=CH₂ | H | tetrahydrofuran-2-yl |
| 4-methoxyphenyl | CH₃ | 4-methylphenyl | H | tetrahydrofuran-2-yl |
| biphenyl-4-yl | CH₃ | 4-chlorophenyl | H | tetrahydrofuran-2-yl |
| 4-phenoxyphenyl | CH₃ | 2,4-difluorophenyl | H | furan-2-yl |
| dicyclohexylmethyl | CH₃ | —(CH₂)₂—CH₃ | H | tetrahydrofuran-3-yl |
| 2,2-dicyclohexylpropyl (bis-cyclohexyl-dimethyl-C) | CH₃ | —(CH₂)₂—CH₃ | H | furan-2-yl |
| thiophen-2-yl | CH₃ | —(CH₂)₂—CH₃ | H | tetrahydrofuran-2-yl |

$$R^1-CH_2-CH(R^2)-CH_2-N(R^3)(CH(R^4)-Het) \quad (I)$$

| $R^1$ | $R^2$ | $R^3$ | $R^4$ | Het |
|---|---|---|---|---|
| 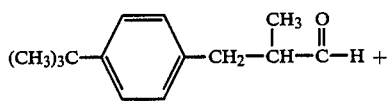 (2-thienyl) | CH₃ | —(CH₂)₂—CH₃ | H | (2-furyl) |
| (2-thienyl) | CH₃ | H | H | (2-thienyl) |

If, for example, 3-(4-t-butylphenyl)-2-methylpropionaldehyde and furanylmethylamine are used as starting materials, the course of the reaction of process (a) according to the invention may be represented by the following equations:

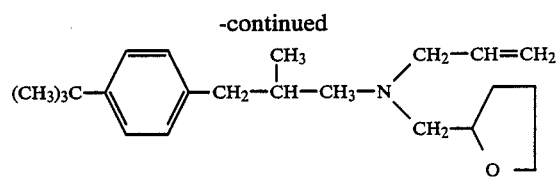

-continued

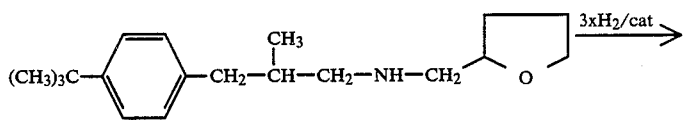

If, for example, 3-(4-t-butylphenyl)-2-methyl-N-(2-tetrahydrofuranylmethyl)-propylamine is used as starting compound, the course of the reaction of process (c) according to the invention may be represented by the following equation:

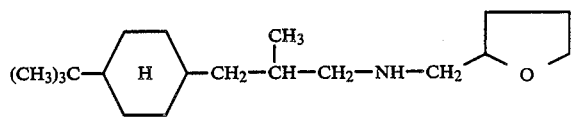

If, for example, 3-(4-t-butylphenyl)-2-methyl-N-(2-tetrahydrofuranylmethyl)-propylamine and allyl bromide are used as starting materials, the course of the reaction of process (b) according to the invention may be represented by the following equation:

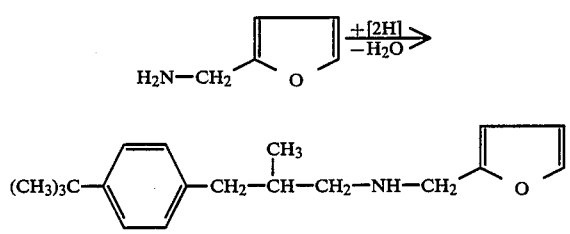

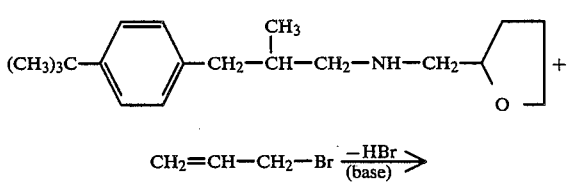

Formula (II) provides a general definition of the substituted aldehydes which are required as starting materials for carrying out process (a) according to the invention. In this formula (II), R¹ and R² preferably represent those radicals which have already been mentioned in connection with the description of the substances of the formula (I) according to the invention as being preferred for these substituents.

The majority of the substituted aldehydes of the formula (II) are known (cf., for example, Can. PA 1,114,286 of 15.12.1981; Japan. JP 48/35065 of 25.10.1973; Japanese Preliminary Published Application JP 55/36454 of 14.03.1980; Japan. JP 47/50,095 of 15.12.1972; Japanese Preliminary Published Application JP 44/9262 of 24.01.1979) or can be prepared analogously to known compounds with the aid of generally known processes (cf., for example, Tetrahedron, 35, 329–340 [1979]; Chem. Lett. 1977, 423–424; J. Org. Chem. 41, 1206–1209 [1976]; J. Amer. Chem. Soc. 108, 7361–7373 [1986]; Bull. Chem. Soc. Japan 46, 3562–3565 [1973] and Org. Prep. Proced. Int. 14, 9–20 [1982]).

Formula (III) provides a general definition of the amines which are furthermore required as starting materials for carrying out process (a) according to the invention. In this formula (III), $R^3$, $R^4$ and Het preferably represent those radicals which have already been mentioned in connection with a description of the substances of the formula (I) according to the invention as being preferred for these substituents.

The amines of the formula (III) are generally known compounds of organic chemistry or can be obtained analogously to generally known processes (cf., for example, J. Prakt. Chem. 317, 897–906 [1975]; DE-OS (German Published Specification) 2,757,922; Ind. J. Chem. B; 193; 310–312 [1980]; Belg. BE 883,713 of 09.12.1980 or Japanese Preliminary Published Application JP 57/2274 of 07.01.1982).

Formula (Ia) provides a general definition of the substituted propylamines which are required as starting materials for carrying out process (b) according to the invention. In this formula (Ia), $R^1$, $R^2$, $R^4$ and Het preferably represent those radicals which have already been mentioned in connection with the description of the substances of the formula (I) according to the invention as being preferred for these substituents.

The substituted propylamines of the formula (Ia) are compounds according to the invention and can be obtained with the aid of processes (a) or (c) according to the invention.

Formula (IV) provides a general definition of the alkylating agents which are furthermore required as starting materials for carrying out process (b) according to the invention. In this formula (IV), $R^{3-1}$ preferably represents straight-chain or branched alkyl having 1 to 8 carbon atoms, in each case straight-chain or branched alkenyl or alkinyl in each case having 3 to 8 carbon atoms, in each case straight-chain or branched alkoxy alkyl, hydroxyalkoxyalkyl or dialkoxyalkyl in each case having 1 to 4 carbon atoms in the individual alkyl parts, straight-chain or branched hydroxyalkyl having 2 to 8 carbon atoms, cycloalkyl having 3 to 7 carbon atoms, cycloalkenyl having 3 to 7 carbon atoms, cycloalkylalkyl having 3 to 7 carbon atoms in the cycloalkyl part and 1 to 8 carbon atoms in the straight-chain or branched alkyl part, cycloalkenylalkyl having 3 to 7 carbon atoms in the cycloalkenyl part and 1 to 8 carbon atoms in the straight-chain or branched alkyl part, furanylmethyl or tetrahydrofuranylmethyl which is in each case optionally monosubstituted to polysubstituted by identical or different, straight-chain or branched alkyl having 1 to 4 carbon atoms, or represents optionally monosubstituted to polysubstituted phenylalkyl having 1 to 4 carbon atoms in the straight-chain or branched alkyl part, the substituents being identical or different and suitable phenyl substituents being: halogen, in each case straight-chain or branched alkyl, alkoxy or alkylthio in each case having 1 to 4 carbon atoms, in each case straight-chain or branched halogenoalkyl, halogenoalkoxy or halogenoalkylthio in each case having 1 to 4 carbon atoms and 1 to 9 identical or different halogen atoms;

$R^{3-1}$ particularly preferably represents methyl, ethyl, n- or i-propyl, n-, i-, s- or t-butyl, in each case straight-chain or branched pentyl, hexyl, heptyl or octyl, represents allyl, butenyl, propargyl, butinyl, methoxyethyl, methoxypropyl, ethoxyethyl, ethoxypropyl, propoxypropyl, dimethoxyethyl, hydroxyethyl, hydroxypropyl, hydroxyethoxyethyl, in each case optionally monosubstituted, disubstituted or trisubstituted cyclohexyl, cyclohexenyl, cyclopentyl, cyclohexylmethyl, cyclohexylethyl, cyclohexenylmethyl, cyclopentylmethyl, furanylmethyl or tetrahydrofuranylmethyl, the substituents being identical or different and suitable substituents being in each case: methyl, ethyl n- or i-propyl, and n-, i-, s- or t-butyl, and in addition represents in each case optionally monosubstituted, disubstituted or trisubstituted benzyl or phenylethyl, the substituents being identical or different and suitable phenyl substituents being in each case: fluorine, chlorine, bromine, methyl, ethyl, n- or i-propyl, methoxy, ethoxy, methylthio, trifluoromethyl, trifluoromethoxy or trifluoromethylthio, $R^{3-1}$ very particularly preferably represents methyl, ethyl, n- or i-propyl, n-, i- or s-butyl, n-pentyl, n-hexyl, n-octyl, allyl, propargyl, methoxyethyl, methoxypropyl, ethoxyethyl or ethoxypropyl.

E preferably represents halogen, in particular chlorine, bromine or iodine, or in each case optionally substituted alkylsulphonyloxy, alkoxysulphonyloxy or arylsulphonyloxy, such as, for example, methanesulphonyloxy, methoxysulphonyloxy or p-toluenesulphonyloxy.

The alkylating agents of the formula (IV) are generally known compounds of organic chemistry.

Formula (Ib) provides a general definition of the substituted propylamines which are required as starting materials for carrying out process (c) according to the invention. In this formula (Ib), $R^2$, $R^3$, $R^4$ and Het preferably represent those radicals which have already been mentioned in connection with the description of the substances of the formula (I) according to the invention as being preferred for these substituents.

$R^{1-1}$ preferably represents in each case optionally monosubstituted to polysubstituted phenyl or naphthyl, the substituents being identical or different and suitable substituents being in each case: halogen, in each case straight-chain or branched alkyl, alkoxy or alkylthio in each case having 1 to 4 carbon atoms, in each case straight-chain or branched halogenoalkyl, halogenoalkoxy or halogenoalkylthio in each case having 1 to 4 carbon atoms and 1 to 9 identical or different halogen atoms, cycloalkyl having 3 to 7 carbon atoms, aryl or aryloxy having 6 to 10 carbon atoms and arylalkyl having 6 to 10 carbon atoms in the aryl part and 1 to 6 carbon atoms in the straight-chain or branched alkyl part which is in each case optionally monosubstituted to polysubstituted by straight-chain or branched alkyl having 1 to 6 carbon atoms, the substituents being identical or different;

$R^{1-1}$ particularly preferably represents in each case optionally monosubstituted, disubstituted or trisubstituted phenyl or naphthyl, the substituents being identical or different and suitable substituents being in each case: fluorine, chlorine, bromine, methyl, ethyl, n- or i-propyl, n-, i-, s- or t-butyl, in each case straight-chain or branched pentyl, hexyl, heptyl, octyl, methoxy, ethoxy, n- or i-propoxy, n-, i-, s- or t-butoxy, methylthio, ethylthio, n- or i-propylthio, trifluoromethoxy, trifluoromethoxy, trifluoromethylthio, cyclohexyl, phenyl, phenoxy, benzyl, 1-phenylethyl, 1-phenylpropyl, 2-phenyl-2-propyl and 2-phenyl-2-butyl.

The substituted propylamines of the formula (Ia) are compounds according to the invention and can be obtained with the aid of process (a) according to the invention.

Suitable diluents for carrying out process (a) according to the invention are inert organic solvents. Polar or dipolar aprotic solvents are preferably used, thus, for example, alcohols, such as methanol, ethanol, n- or i-propanol, esters, such as ethyl acetate, or ethers, such as diethyl ether, dioxane or tetrahydrofuran.

Suitable reducing agents for carying our process (a) according to the invention are all reducing agents which can conventionally be used for such reductive aminations. The preferred reducing agents are molecular hydrogen in the presence of a suitable hydrogenation catalyst, or formic acid.

Suitable catalysts for carrying out process (a) according to the invention are conventional hydrogenation catalysts. Noble metal catalysts, such as palladium, platinum or platinum oxide, if appropriate in the presence of a suitable support, such as, for example, charcoal, aluminum oxide or silicon dioxide, are preferably used.

The reaction temperatures can be varied within a relatively wide range when carrying out process (a) according to the invention. In general, the process is carried out at temperatures between 20° C. and 250° C., preferably at temperatures between 50° C. and 150° C.

Process (a) according to the invention is, if appropriate, carried out under increased pressure. In general, the process is carried out in a pressure range between 1 and 150 bar, preferably between 20 and 100 bar.

To carry out process (a) according to the invention, 1.0 to 3.0 moles, preferably equimolar amounts, of amine of the formula (III), 1.0 to 20.0 moles of reducing agent and, if appropriate, 0.001 to 0.1 mole of catalyst are generally employed per mole of substituted aldehyde of the formula (II). The reaction is carried out and the reaction products are worked up and isolated by generally known, conventional methods (cf., for example, "Organikum" [Practical Organic Chemistry], 15th edition, p. 542, VEB Deutscher Verlag der Wissenschaften Berlin 1981).

In a variant for carrying out the reaction of process (a) according to the invention, it is also possible to prepare the aldehydes of the formula (II) which are suitable starting compounds directly in the reaction vessel in a prior reaction ("one-pot reaction"), by condensing generally known aldehydes of the formula (V)

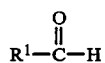  (V)

in which
R$^1$ has the abovementioned meaning, with likewise generally known aldehydes of the formula (VI)

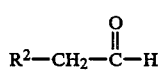  (VI)

in which
R$^2$ has the abovementioned meaning, in the presence of a base, such as, for example, sodium hydroxide, and if appropriate in the presence of a diluent, such as, for example, methanol, at temperatures between 0° C. and 80° C. ("aldol condensation"), and further reacting the reaction mixture thus obtainable directly with amines of the formula (III) in the presence of a reducing agent in accordance with process (a) according to the inventinon (in this respect cf., for example, DE-OS (German Published Specification) 3,105,446).

Suitable diluents for carrying out process (b) according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Process (b) according to the invention can also be carried out, if appropriate, in a two-phase system, such as, for example, water/toluene or water/dichloromethane, if appropriate in the presence of a phase-transfer catalyst. Examples of such catalysts which may be mentioned are: tetrabutylammonium iodide, tetrabutylammonium bromide, tributyl-methylphosphonium bromide, trimethyl-C$_{13}$/C$_{15}$-alkylammonium chloride, dibenzyl-dimethylammonium methylsulphate, dimethyl-C$_{12}$/C$_{14}$-alkyl-benzylammonium chloride, tetrabutylammonium hydroxide, 15-crown-5, 18-crown-6, triethylbenzylammonium chloride and trimethylbenzylammonium chloride.

Suitable reaction auxiliaries for carrying out process (b) according to the invention are all inorganic and organic bases which can conventionally be used. Alkali metal hydrides, hydroxides, amides, carbonates or bicarbonates, such as, for example, sodium hydride, sodium amide, sodium hydroxide, sodium carbonate or sodium bicarbonate, or alternatively tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU), are preferably used.

The reaction temperatures may be varied within a relatively wide range when carrying out process (b) according to the invention. In general, the process is carried out at temperatures between $-20°$ C. and $+150°$ C., preferably at temperatures between 0° C. and $+100°$ C.

To carry out process (b) according to the invention, 1.0 to 20.0 moles, preferably 1.0 to 15.0 moles, of alkylating agent of the formula (IV) and, if appropriate, 1.0 to 3.0 moles, preferably 1.0 to 2.0 moles, of reaction auxiliary and, if appropriate, 0.01 to 1.0 mole of phase-transfer catalyst are generally employed per mole of substituted propylamine of the formula (Ia). The reaction is carried out and the reaction products of the formula (I) are worked up and isolated in a generally conventional fashion.

Suitable diluents for carrying out process (c) according to the invention are inert organic solvents. These preferably include aliphatic hydrocarbons, such as petroleum ether, hexane or cyclohexane, ethers, such as diethyl ether, dioxane, tetrahydrofuran or ethylene glycol dimethyl or diethyl ether; esters, such as ethyl acetate; sulphoxides, such as dimethyl sulphoxide; and alcohols, such as methanol or ethanol.

Suitable catalysts for carrying out process (c) according to the invention are conventional hydrogenation catalysts. Noble metal, noble metal oxide or noble metal hydroxide catalysts or so-called Raney catalysts, such as, in particular, platinum, platinum oxide, nickel and ruthenium, if appropriate on a suitable support, such as charcoal, aluminum oxide or silicon dioxide, are preferably used.

The reaction temperatures may be varied within a relatively wide range when carrying out process (c) according to the invention. In general, the process is carried out at temperatures between 20° C. and 250° C., preferably at temperatures between 20° C. and 200° C.

Process (c) according to the invention may be carried out at atmospheric pressure or alternatively at increased pressure. In general, the process is carried out between 1 atm and 300 atm, preferably between 1 atm and 200 atm.

To carry out process (c) according to the invention, 0.001 to 0.1 mole of hydrogenation catalyst are added per mole of substituted propylamine of the formula (Ib), and hydrogen is introduced into an autoclave until the necessary pressure has been reached. The reaction is carried out and the reaction products of the formula (I) are worked up and isolated analogously to generally known processes (cf., for example, DE-OS (German Published Specification) 2,752,135).

The following acids are preferably suitable for preparing plant-tolerated acid-addition salts of the compounds of the formula (I): hydrohalic acids, such as, for example, hydrochloric acid and hydrobromic acid, in particular hydrochloric acid, furthermore phosphoric acid, nitric acid, sulphuric acid, mono-, bi- and trifunctional carboxylic acids and hydroxycarboxylic acids, such as, for example, formic acid, acetic acid, maleic acid, succinic acid, fumaric acid, tartaric acid, citric acid, salicylic acid, sorbic acid and lactic acid; sulphonic acids, such as, for example, p-toluenesulphonic acid and 1,5-naphthalenedisulphonic acid, and also saccharin.

The acid-addition salts of the compounds of the formula (I) can be obtained in a simple fashion by conventional salt-formation methods, such as, for example, by dissolving a compound of the formula (I) in a suitable inert solvent and adding the acid, such as, for example, hydrochloric acid, and can be isolated in a known fashion, for example by filtering off, and, if appropriate, purified by washing with an inert organic solvent.

The active compounds according to the invention have a strong action against pests and can be employed in practice for combating undesired harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Pythium species, such as, for example, Pythium ultimum; Phytophthora species, such as, for example, Phytophthora infestans; Pseudoperonospora species, such as, for example, Pseudoperonospora humuli or Pseudoperonospora cubensis; Plasmopara species, such as, for example, Plasmopara viticola; Peronospora species, such as, for example, Peronospora pisi or P. brassicae; Erysiphe species, such as, for example, Erysiphe graminis; Sphaerotheca species, such as, for example, Sphaerotheca fuliginea; Podosphaera species, such as, for example, Podosphaera leucotricha; Venturia species, such as, for example, Venturia inaequalis; Pyrenophora species, such as, for example, Pyrenophora teres or P. graminea (conidia form: Drechslera, syn: Helminthosporium); Cochliobolus species, such as, for example, Cochliobolus sativus (conidia form: Drechslera, syn: Helminthosporium); Uromyces species, such as, for example, Uromyces appendiculatus; Puccinia species, such as, for example, Puccinia recondita; Tilletia species, such as, for example, Tilletia caries; Ustilago species, such as, for example, Ustilago nuda or Ustilago avenae; Pellicularia species, such as, for example, Pellicularia sasakii; Pyricularia species, such as, for example, Pyricularia oryzae; Fusarium species, such as, for example, Fusarium culmorum; Botrytis species, such as, for example, Botrytis cinerea; Septoria species, such as, for example, Septoria nodorum; Leptosphaeria species, such as, for example, Leptosphaeria nodorum; Cercospora species, such as, for example, Cercospora canescens; Alternaria species, such as, for example, Alternaria brassicae and Pseudocercosporella species, such as, for example, Pseudocercosporella herpotrichoides.

The good toleration, by plants, of the active compounds, at the concentrations required for combating plant diseases, permits treatment of above-ground parts of plants, of vegetative propagation stock and seeds, and of the soil.

At the same time, the active compounds according to the invention can be employed particularly successfully for combating cereal diseases, such as, for example against the pathogen of glume blotch in wheat (Leptosphaeria nodorum), or against the pathogens of rust and mildew in cereals, and for combating rice diseases, such as, for example, against the pathogen of rice lichen disease (Pyricularia oryzae).

In addition, the active compounds according to the invention also exhibit an insecticidal activity and can be employed, for example, for combating leaf insecticides.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

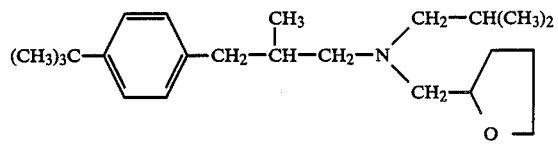

(Process a)

A solution of 4.7 g (0.03 mol) of N-isobutyltetrahydrofuran-2-yl-methylamine (cf. German Pat. No. 1,278,443) and 6.1 g (0.03 mol) of 3-(4-t-butylphenyl)-2-methyl-propionaldehyde (cf., for example, EP 58,326) in 100 ml of methanol is hydrogenated for 3 hours at 100° C. and at a hydrogen pressure of 50 bar together with 2 g of palladium on aluminum oxide (1%). For work-up, the catalyst is filtered off and the solvent is removed by distillation.

9.5 g (92% of theory) of [3-(4-t-butylphenyl)-2-methyl]-N-isobutyl-N-tetrahydrofuran-2-yl-methyl-propylamine are obtained as an oil with a purity, determined by gas chromatography, of 95%.

$^1$H NMR (CDCl$_3$/tetramethylsilane) δ=3.65–4.0 (m, 3H); 1.3 (s, 9H) ppm.

The following substituted propylamines of the general formula (I) are obtained in a corresponding fashion and according to the general instructions for the preparation:

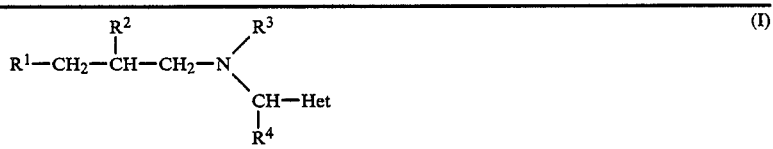

| Ex. No. | R$^1$ | R$^2$ | R$^3$ | R$^4$ | Het | Physical properties |
|---|---|---|---|---|---|---|
| 2 | (CH$_3$)$_3$C-⌬- | CH$_3$ | CH$_3$ | H | [CH$_3$, O tetrahydrofuran-2-yl with 2-CH$_3$] | $^1$H NMR*: 1.3; 3.75–3.9 |
| 3 | (CH$_3$)$_3$C-⌬- | CH$_3$ | CH$_3$—(CH$_2$)$_2$— | H | [tetrahydrofuran-2-yl] | $^1$H NMR*: 1.3; 3.7–4.0 |

-continued $$R^1-CH_2-\underset{R^2}{CH}-CH_2-\underset{\underset{\underset{R^4}{CH-Het}}{|}}{N}-R^3 \quad (I)$$

| Ex. No. | R¹ | R² | R³ | R⁴ | Het | Physical properties |
|---|---|---|---|---|---|---|
| 4 | (CH₃)₃C—C₆H₄— | CH₃ | CH₃ | H | tetrahydrofuran-2-yl | ¹H NMR*: 1.3; 3.65–4.05 |
| 5 | (CH₃)₃C—C₆H₄— | CH₃ | (CH₃)₂CH— | H | tetrahydrofuran-2-yl | ¹H NMR*: 1.3; 3.70–3.95 |
| 6 | (CH₃)₃C—C₆H₄— | CH₃ | cyclohexyl-CH₂— | H | tetrahydrofuran-2-yl | ¹H NMR*: 1.3; 3.7–4.0 |
| 7 | (CH₃)₃C—C₆H₄— | CH₃ | CH₃ | H | 5-methyl-tetrahydrofuran-2-yl | ¹H NMR*: 1.3; 3.9–4.0 |
| 8 | (CH₃)₃C—C₆H₄— | CH₃ | (tetrahydrofuran-2-yl)-CH₂— | H | 2-methyl-tetrahydrofuran-2-yl | ¹H NMR*: 1.3; 3.6–4.0 |
| 9 | (CH₃)₃C—C₆H₄— | CH₃ | (2-methyl-tetrahydrofuran-2-yl)-CH₂— | H | 2-methyl-tetrahydrofuran-2-yl | ¹H NMR*: 1.3; 3.7–3.9 |
| 10 | (CH₃)₃C—C₆H₄— | CH₃ | (tetrahydrofuran-2-yl)-CH₂— | H | tetrahydrofuran-2-yl | ¹H NMR*: 1.3; 3.65–4.0 |
| 11 | (CH₃)₃C—C₆H₄— | CH₃ | CH₃(CH₂)₂— | H | tetrahydropyran-2-yl | ¹H NMR*: 1.3; 3.25–3.45 |
| 12 | (CH₃)₃C—C₆H₄— | CH₃ | H | H | tetrahydrofuran-2-yl | ¹H—NMR*: 1.3; 3.7–4.05 |
| 13 | (CH₃)₃C—C₆H₄— | CH₃ | H | H | tetrahydrofuran-2-yl | Mp. 142° C. (hydrochloride) |
| 14 | (CH₃)₃C—C₆H₁₀— | CH₃ | —(CH₂)₂—CH₃ | H | tetrahydrofuran-2-yl | ¹H—NMR*: 0.8; 3.7–4.1 |
| 15 | (CH₃)₃C—C₆H₄— | CH₃ | —C₂H₅ | H | tetrahydrofuran-2-yl | ¹H—NMR*: 1.3; 3.7–4.05 |

-continued

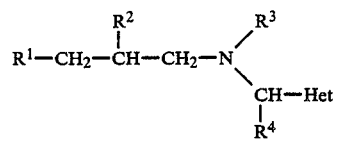

| Ex. No. | R¹ | R² | R³ | R⁴ | Het | Physical properties |
|---|---|---|---|---|---|---|
| 16 | (CH₃)₃C—C₆H₄— | CH₃ | —(CH₂)₃—CH₃ | H | 2-tetrahydrofuryl | ¹H—NMR*: 1.4; 3.65–4.0 |
| 17 | (CH₃)₃C—C₆H₄— | CH₃ | —(CH₂)₇—CH₃ | H | 2-tetrahydrofuryl | ¹H—NMR*: 1.3; 3.6–4.0 |
| 18 | (CH₃)₃C—C₆H₄— | CH₃ | cyclohexyl | H | 2-tetrahydrofuryl | ¹H—NMR*: 1.3; 3.65–3.95 |
| 19 | (CH₃)₃C—C₆H₄— | CH₃ | CH(CH₃)—C₂H₅ | H | 2-tetrahydrofuryl | ¹H—NMR*: 1.3; 3.7–3.95 |
| 20 | (CH₃)₃C—C₆H₄— | CH₃ | —(CH₂)₂—CH₃ | H | 5-methyl-2-tetrahydrofuryl linked via phenyl with o-NHC(O)CH₃ and SO₂ | ¹H—NMR*: 1.3; 7.1; 7.3; 7.6; 7.8; |
| 21 | (CH₃)₃C—C₆H₄— | CH₃ | phenyl | H | 2-tetrahydrofuryl | ¹H—NMR*: 1.3; 3.7–4.15 |
| 22 | (CH₃)₃C—C₆H₄— | CH₃ | —CH₂—CH₂—OCH₃ | H | 2-tetrahydrofuryl | ¹H—NMR*: 1.3; 3.65–4.0 |
| 23 | (CH₃)₃C—C₆H₄— | CH₃ | —(CH₂)₃—OCH₃ | H | 2-tetrahydrofuryl | ¹H—NMR*: 1.3; 3.65–4.0 |
| 24 | (CH₃)₃C—C₆H₄— | CH₃ | —(CH₂)₂—CH₃ | H | 3-tetrahydrofuryl | ¹H—NMR*: 1.3; 3.5–3.9 |
| 25 | (CH₃)₃C—C₆H₄— | CH₃ | —(CH₂)₃—O₂H₅ | H | 2-tetrahydrofuryl | ¹H—NMR*: 1.3; 3.7–4.0 |
| 26 | (CH₃)₃C—C₆H₄— | CH₃ | —CH₂—CH=CH₂ | H | 2-tetrahydrofuryl | ¹H—NMR*: 1.3; 3.7–4.0 |

-continued

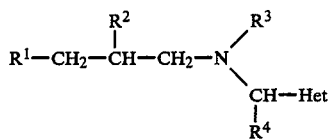

(I)

| Ex. No. | R¹ | R² | R³ | R⁴ | Het | Physical properties |
|---|---|---|---|---|---|---|
| 27 | (CH₃)₃C-⟨phenyl⟩- | CH₃ | -CH₂-⟨phenyl⟩ | H | ⟨tetrahydrofuran-2-yl⟩ | $^1$H—NMR*: 1.3; 3.65–4.05 |
| 28 | (CH₃)₃C-⟨cyclohexyl-H⟩- | CH₃ | -C₂H₅ | H | ⟨tetrahydrofuran-2-yl⟩ | $^1$H—NMR*: 0.8; 3.6–4.05 |
| 29 | (CH₃)₃C-⟨cyclohexyl-H⟩- | CH₃ | -(CH₂)₃-CH₃ | H | ⟨tetrahydrofuran-2-yl⟩ | $^1$H—NMR*: 0.8; 3.65–4.0 |
| 30 | (CH₃)₃C-⟨cyclohexyl-H⟩- | CH₃ | -CH(CH₃)-C₂H₅ | H | ⟨tetrahydrofuran-2-yl⟩ | $^1$H—NMR*: 0.8; 3.65–3.9 |
| 31 | (CH₃)₃C-⟨cyclohexyl-H⟩- | CH₃ | -(CH₂)₃-OCH₃ | H | ⟨tetrahydrofuran-2-yl⟩ | $^1$H—NMR*: 0.8; 3.65–3.95 |
| 32 | (CH₃)₃C-⟨cyclohexyl-H⟩- | CH₃ | -(CH₂)₂-CH₃ | H | ⟨tetrahydrofuran-2-yl⟩ | $^1$H—NMR*: 0.8; 3.7–3.9 |
| 33 | (CH₃)₃C-⟨phenyl⟩- | CH₃ | H | H | ⟨tetrahydrofuran-O-benzisothiazolone⟩ | $^1$H—NMR*: 1.3; 7.1; 7.3; 7.6; 7.8; |
| 34 | (CH₃)₃C-⟨phenyl⟩- | CH₃ | C₂H₅ | H | ⟨tetrahydrofuran-O-benzisothiazolone⟩ | $^1$H—NMR*: 1.3; 7.1; 7.3; 7.6; 7.8; |
| 35 | (CH₃)₃C-⟨phenyl⟩- | CH₃ | -(CH₂)₃-CH₃ | H | ⟨tetrahydrofuran-O-benzisothiazolone⟩ | $^1$H—NMR*: 1.3; 7.1; 7.3; 7.6; 7.8; |
| 36 | (CH₃)₃C-⟨phenyl⟩- | CH₃ | -(CH₂)₇-CH₃ | H | ⟨tetrahydrofuran-O-benzisothiazolone⟩ | $^1$H—NMR*: 1.3; 7.1; 7.3; 7.6; 7.8; |

-continued

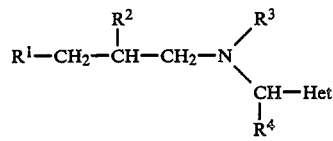
(I)

| Ex. No. | R¹ | R² | R³ | R⁴ | Het | Physical properties |
|---|---|---|---|---|---|---|
| 37 | (CH₃)₃C-C₆H₄- | CH₃ | cyclohexyl | H | tetrahydrofuran-phenyl (o-C(O)-, o-SO₂NH-) | ¹H—NMR*: 1.3; 7.1; 7.3; 7.6; 7.8; |
| 38 | (CH₃)₃C-C₆H₄- | CH₃ | -CH(CH₃)-C₂H₅ | H | tetrahydrofuran-phenyl | ¹H—NMR*: 1.3; 7.1; 7.3; 7.6; 7.8; |
| 39 | (CH₃)₃C-C₆H₄- | CH₃ | -(CH₂)₃-OCH₃ | H | tetrahydrofuran-phenyl | ¹H—NMR*: 1.3; 7.1; 7.3; 7.6; 7.8; |
| 40 | (CH₃)₃C-C₆H₄- | CH₃ | -(CH₂)₂-CH₃ | H | tetrahydrofuran-phenyl | ¹H—NMR*: 1.3; 7.1; 7.3; 7.6; 7.8; |
| 41 | (CH₃)₃C-cyclohexyl | CH₃ | -(CH₂)₂-OCH₃ | H | tetrahydrofuran-phenyl | ¹H—NMR*: 0.8; 3.6–4.0 |
| 42 | (CH₃)₃C-cyclohexyl | CH₃ | -(CH₂)₃-OC₂H₅ | H | tetrahydrofuran-phenyl | ¹H—NMR*: 0.8; 3.7–4.0 |
| 43 | (CH₃)₃C-C₆H₄- | CH₃ | -CH₂-CH=CH₂ | H | tetrahydrofuran-phenyl | ¹H—NMR*: 1.3; 7.1; 7.3; 7.6; 7.8; |
| 44 | (CH₃)₃C-cyclohexyl | CH₃ | -(CH₂)₂-CH₃ | H | tetrahydrofuran-phenyl | ¹H—NMR*: 0.8; 7.6; 7.8 |
| 45 | (CH₃)₃C-C₆H₄- | CH₃ | phenyl | H | tetrahydrofuran-phenyl | ¹H—NMR*: 1.3; 6.6; 7.0–7.3; 7.6–7.9 |

-continued $$R^1-CH_2-\underset{R^2}{\underset{|}{CH}}-CH_2-\underset{\underset{CH-Het}{\underset{|}{R^4}}}{N}-R^3 \qquad (I)$$

| Ex. No. | $R^1$ | $R^2$ | $R^3$ | $R^4$ | Het | Physical properties |
|---|---|---|---|---|---|---|
| 46 | (CH₃)₃C—⟨C₆H₄⟩— | CH₃ | —(CH₂)₂—OCH₃ | H | tetrahydrofuran-2-yl × 2-acyl-benzenesulfonamide (cyclic) | ¹H—NMR*: 1.3; 7.1; 7.3; 7.6; 7.8; |
| 47 | (CH₃)₃C—⟨C₆H₄⟩— | CH₃ | —(CH₂)₃—OC₂H₅ | H | tetrahydrofuran-2-yl × 2-acyl-benzenesulfonamide (cyclic) | ¹H—MMR*: 1.3; 7.1; 7.3; 7.6; 7.8 |
| 48 | (CH₃)₃C—⟨C₆H₄⟩— | CH₃ | —CH₂—C≡CH | H | tetrahydrofuran-2-yl | ¹H—NMR*: 1.3; 3.7–4.0 |
| 49 | (CH₃)₃C—⟨C₆H₄⟩— | CH₃ | —CH₂—⟨C₆H₅⟩ | H | tetrahydrofuran-2-yl × 2-acyl-benzenesulfonamide (cyclic) | ¹H—NMR*: 1.3; 7.1; 7.3–7.4; 7.6; 7 |
| 50 | (CH₃)₃C—⟨C₆H₁₀⟩— | CH₃ | —(CH₂)₂—OCH₃ | H | tetrahydrofuran-2-yl × 2-acyl-benzenesulfonamide (cyclic) | ¹H—NMR* 0.8; 7.6; 7.8 |
| 51 | (CH₃)₃C—⟨C₆H₁₀⟩— | CH₃ | —(CH₂)₃—OC₂H₅ | H | tetrahydrofuran-2-yl × 2-acyl-benzenesulfonamide (cyclic) | ¹H—NMR*: 0.8; 7.6; 7.8 |
| 52 | (CH₃)₃C—⟨C₆H₁₀⟩— | CH₃ | —CH(CH₃)—C₂H₅ | H | tetrahydrofuran-2-yl × 2-acyl-benzenesulfonamide (cyclic) | ¹H—NMR*: 0.8; 7.6; 7.8 |
| 53 | (CH₃)₃C—⟨C₆H₁₀⟩— | CH₃ | —(CH₂)₂—OCH₃ | H | tetrahydrofuran-2-yl × 2-acyl-benzenesulfonamide (cyclic) | ¹H—NMR*: 0.8; 7.6; 7.8 |
| 54 | (CH₃)₃C—⟨C₆H₁₀⟩— | CH₃ | —(CH₂)₂—CH₃ | H | tetrahydrofuran-2-yl × 2-acyl-benzenesulfonamide (cyclic) | ¹H—NMR*: 0.8; 7.6; 7.8 |
| 55 | (CH₃)₃C—⟨C₆H₄⟩— | CH₃ | —(CH₂)₂—CH₃ | H | thien-2-yl | ¹H—NMR*: 6.7; 6.8; 7.05; 7.15 7.3 |

-continued
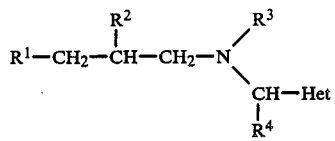
(I)
| Ex. No. | R¹ | R² | R³ | R⁴ | Het | Physical properties |
|---|---|---|---|---|---|---|
| 56 | 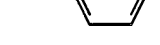 | CH₃ | —CH₂—C≡CH | H |  | ¹H—NMR*: 1.3; 7.1; 7.3; 7.6; 7.8 |
| 57 | 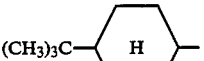 | CH₃ | CH₃ | H |  | ¹H—NMR*: 1.3; 3.7–4.0 |
| 58 | 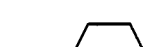 | CH₃ | CH₃ | H |  | ¹H—NMR*: 0.8; 7.6; 7.8 |
| 59 |  | CH₃ | C₂H₅ | H | 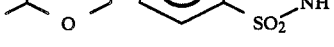 | ¹H—NMR*: 0.8; 7.6; 7.8 |
| 60 | 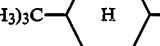 | CH₃ | —(CH₂)₃—CH₃ | H |  | ¹H—NMR*: 0.8; 7.6; 7.8 |
| 61 | 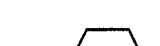 | CH₃ | —(CH₂)₂—CH₃ | H |  | ¹H—NMR*: 1.3; 3.9–4.05 |
| 62 | 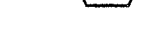 | CH₃ | —(CH₂)₂—CH₃ | H | 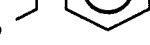 | ¹H—NMR*: 1.3; 3.6–3.9 |
| 63 | 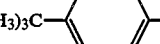 | CH₃ | —(CH₂)₂—CH₃ | H | 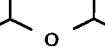 | ¹H—NMR*: 0.8; 3.7–4.0 |
| 64 |  | CH₃ | —(CH₂)₂—CH₃ | H | 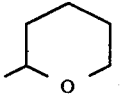 | ¹H—NMR*: 1.3; 3.5 |
| 65 |  | CH₃ | —(CH₂)₂—CH₃ | H |  | ¹H—NMR*: 1.3; 7.1; 7.3 |

-continued

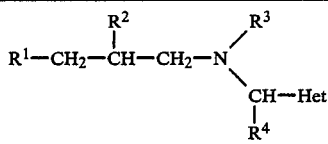
(I)

| Ex. No. | R¹ | R² | R³ | R⁴ | Het | Physical properties |
|---|---|---|---|---|---|---|
| 66 | (CH₃)₃C-C₆H₄- | CH₃ | —(CH₂)₂—CH₃ | H | (furan) | ¹H—NMR*: 6.1; 6.2; 6.3; 7.05; 7.25; 7.35 |
| 67 | (CH₃)₃C-C₆H₄- | CH₃ | —(CH₂)₂—CH₃ | H | tetrahydrofuryl-CH₃ × benzo[sulfonamide ketone] | ¹H—NMR*: 1.3; 7.1; 7.3; 7.6; 7.8 |
| 68 | (CH₃)₃C-C₆H₁₀- | CH₃ | —(CH₂)₂—CH₃ | H | tetrahydrofuryl × benzo[sulfonamide ketone] | ¹H—NMR*: 0.8; 7.7–8.0 |
| 69 | (CH₃)₃C-C₆H₁₀- | CH₃ | —(CH₂)₂—CH₃ | H | 2,5-dimethyltetrahydrofuryl | ¹H—NMR*: 0.8; 3.8–4.0 |
| 70 | (CH₃)₃C-C₆H₄- | CH₃ | —(CH₂)₂—CH₃ | H | 2-chlorothienyl (methyl) | ¹H—NMR*: 1.3; 4.2–4.5; 7.6; 7.8 |
| 71 | (CH₃)₃C-C₆H₁₀- | CH₃ | —(CH₂)₂—CH₃ | H | tetrahydrofuryl-CH₃ × benzo[sulfonamide ketone] | ¹H—NMR*: 4.0; 4.3; 7.6; 7.8 |
| 72 | (CH₃)₃C-C₆H₄- | CH₃ | —(CH₂)₂—CH₃ | H | thienyl | ¹H—NMR*: 1.3; 4.5–4.8; 7.6; 7.8 |
| 73 | (CH₃)₃C-C₆H₄- | CH₃ | —(CH₂)₂—CH₃ | H | furyl | ¹H—NMR*: 1.3; 4.3–4.5; 7.6; 7.7–7.8 |
| 74 | (CH₃)₃C-C₆H₄- | CH₃ | —(CH₂)₂—CH₃ | H | 2,5-dichlorothienyl | ¹H—NMR*: 1.3; 4.2–4.7 |
| 75 | (CH₃)₃C-C₆H₁₀- | CH₃ | H | H | tetrahydrofuryl | ¹H—NMR*: 8.8; 3.6–4.1 |

*The ¹H NMR spectra were recorded in deuterochloroform (CDl₃) using tetramethylsilane (TMS) as the internal standard. The chemical shift is given as the δ value in ppm.

USE EXAMPLES

In the following use examples, the compound shown below was employed as comparison substance:

(A)

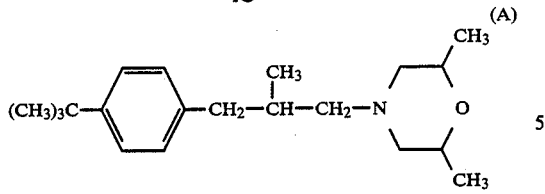

1-(4-t-butylphenyl)-2-methyl-3-(2,6-dimethylmorpholin-4-yl)-propane (known from DE-OS (German Published Specification) 2,656,747).

EXAMPLE A

Leptosphaeria nodorum test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test the protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 3 and 7.

It is understood that the specification and examples are illustrative but not limitative of the present invention and that other embodiments within the spirit and scope of the invention will suggest themselves to those skilled in the art.

We claim:

1. A substituted propylamine of the formula 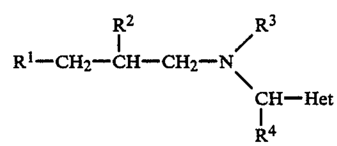 (I)

in which $R^1$ represents in each case optionally monosubstituted to polysubstituted cycloalkyl or cycloalkenyl in each case having 3 to 10 carbon atoms, the substituents being independently selected from the group consisting of straight-chain or branched alkyl having 1 to 8 carbon atoms or cycloalkylalkyl having 1 to 8 carbon atoms in the straight-chain or branched alkyl part and 3 to 7 carbon atoms in the cycloalkyl part; or it represents in each case optionally monosubstituted to polysubstituted tetrahydronaphthyl or decahydronaphthyl, the substituents being identical or different and being: in each case straight-chain or branched alkyl or alkoxy in each case having 1 to 8 carbon atoms; or represents in each case monosubstituted to polysubstituted phenyl or naphthyl, the substituents being independently selected from the group consisting of halogen, straight-chain or branched alkyl having 1 to 8 carbon atoms, in each case straight-chain or branched alkoxy or alkylthio in each case having 1 to 4 carbon atoms, in each case straight-chain or branched halogenoalkyl, halogenoalkoxy or halogenoalkylthio in each case having 1 to 4 carbon atoms and 1 to 9 identical or different halogen atoms, cycloalkyl having 3 to 7 carbon atoms, aryl or aryloxy having 6 to 10 carbon atoms which is in each case optionally monosubstituted to polysubstituted by identical or different, straight-chain or branched alkyl having 1 to 6 carbon atoms, and arylalkyl having 6 to 10 carbon atoms in the aryl part and 1 to 6 carbon atoms in the straight-chain or branched alkyl part; or represents optionally monosubstituted to polysubstituted thienyl, the substituents being independently selected from the group consisting of halogen, in each case straight-chain or branched alkyl or halogenoalkyl in each case having 1 to 8 carbon atoms and 1 to 9 identical or different halogen atoms;

$R^2$ represents straight-chain or branched alkyl having 1 to 4 carbon atoms, $R^3$ represents hydrogen, straight-chain or branched alkyl having 1 to 8 carbon atms, in each case straight-chain or branched alkenyl or alkynyl in each case having 3 to 8 carbon atoms, in each case straight-chain or branched alkoxyalkyl, hydroxyalkoxyalkyl or dialkoxyalkyl in each case having 1 to 4 carbon atoms in the individual alkyl parts, straight-chain or branched hydroxyalkyl having 2 to 8 carbon atoms, cyano, formyl, cycloalkyl having 3 to 7 carbon atoms, cycloalkenyl having 3 to 7 carbon atoms, cycloalkylalkyl having 3 to 7 carbon atoms in the cycloalkyl part and 1 to 8 carbon atoms in the straight-chain or branched alkyl part, cycloalkenylalkyl having 3 to 7 carbon atoms in the cycloalkenyl part and 1 to 8 carbon atoms in the straight-chain or branched alkyl part, furanylmethyl or tetrahydrofuranylmethyl which is in each case optionally monosubstituted to polysubstituted by identical or different straight-chain or branched alkyl having 1 to 4 carbon atoms, or represents phenylalkyl having 1 to 4 carbon atoms in the straight-chain or branched alkyl part or phenyl which is in each case optionally monosubstituted to polysubstituted by substituents, the phenyl substituents being independently selected from the group consisting of halogen, in each case straight-chain or branched alkyl, alkoxy or alkylthio in each case having 1 to 4 carbon atoms, and in each case straight-chain or branched halogenoalkyl, halogenoalkoxy or halogenoalkylthio in each case having 1 to 4 carbon atoms and 1 to 9 identical or different halogens, $R^4$ represents hydrogen or straight-chain or branched alkyl having 1 to 4 carbon atoms, and Het represents an in each case monosubstituted to polysubstituted heterocyclic ring of the formula

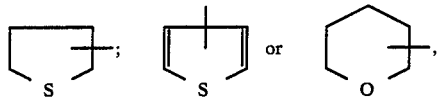

the substituents being independently selected from the group consisting of in each case straight-chain or branched alkyl, alkoxy, alkylthio or alkoxycarbonyl in each case having 1 to 4 carbon atoms in the individual alkyl parts, and in each case straight-chain or branched halogenoalkyl, halogenoalkoxy or halogeneoalkylthio in each case having 1 to 4 carbon atoms and 1 to 9 identical or different halogen atoms, or an acid-addition salt thereof.

2. A substituted propylamine or salt according to claim 1 in which $R^1$ represents in each case optionally monosubstituted, disubstituted or trisubstituted cyclohexyl or cyclohexenyl, the substituents being independently selected from the group consisting of methyl, ethyl, n- or i-propyl, n-, i-, s- or t-butyl, straight-chain or branched pentyl, straight-chain or branched hexyl, cyclohexyl-methyl, 1-cyclohexyl-ethyl-, 1-cyclohexylpropyl, 1-cyclohexylbutyl, 2-cyclohexyl-2-propyl and 2-cyclohexyl-2-butyl; or represents optionally monosubstituted, disubstituted or trisubstituted tetrahydronaphthyl or decahydronaphthyl, the substituents being independently selected from the group consisting of methyl, ethyl, n- or i-propyl, n-, i-, s- or t-butyl, straight-chain or branched pentyl, methoxy, ethoxy, n- or i-propoxy; or represents in each case optionally monosubstituted, disubstituted or trisubstituted phenyl or naphthyl, the substituents being independently selected from the group consisting of fluorine, chlorine, bromine, methyl, ethyl, n- or i-propyl, n-, i-, s- or t-butyl, in each case straight-chain or branched pentyl, hexyl, heptyl or octyl, methoxy, ethoxy, n- or i-propoxy, n-, i-, s- or t-butoxy, methylthio, ethylthio, n- or i-propylthio, trifluoromethyl, trifluoromethoxy, trifluoromethylthio, cyclohexyl, phenyl, phenoxy, benzyl, 1-phenylethyl, 1-phenylpropyl, 2-phenyl-2-propyl and 2-phenyl-2-butyl, or represents 2-thienyl or 3-thienyl which is in each case optionally monosubstituted, disbustituted or trisubstituted by fluorine, chlorine, bromine, methyl, ethyl, n-or i-propyl, n- or i-, s- or t-butyl or trifluoromethyl, the substituents being identical or different;

$R^2$ represents methyl, ethyl, n- or i-propyl, $R^3$ represents hydrogen, methyl, ethyl, n- or i-propyl, n-, i-, s- or t-butyl, in each case straight-chain or branched pentyl, hexyl, heptyl or octyl, represent allyl, butenyl, propargyl, butynyl, methoxyethyl, methoxypropyl, ethoxyethyl, ethoxypropyl, propoxypropyl, dimethoxyethyl, hydroxyethyl, hydroxypropyl, hydroxyethoxyethyl, in each case optionally monosubstituted, disubstituted or trisubstituted cyclohexyl, cyclohexenyl, cyclopentyl, cyclohexylmethyl, cyclohexylethyl, cyclohexenylmethyl, cyclopentylmethyl, furanylmethyl or tetrahydrofuranylmethyl, the substituents being independently selected from the group consisting of methyl, ethyl, n- or i-propyl, n-, i-, s- or t-butyl; or represents in each case optionally monosubstituted, disubstituted or trisubstituted benzyl, phenylethyl or phenyl, the substituents being identical or different and suitable phenyl substituents being in each case: fluorine, chlorine, bromine, methyl, ethyl, n- or i-propyl, methoxy, ethoxy, methylthio, trifluoromethyl, trifluoromethoxy or trifluoromethylthio, $R^4$ represents hydrogen, methyl, ethyl, n- or i-propyl, and Het represents an in each case optionally monosubstituted, disubstituted or trisubstituted heterocyclic ring of the formula

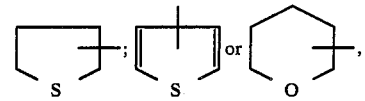

the substituents being independently selected from the group consisting of methyl, ethyl, n- or i-propyl, n-, i-, s- or t-butyl, methoxy, ethoxy, n- or i-propoxy or methylthio.

3. A substituted propylamine or salt according to claim 1, in which $R^1$ represents in each case optionally monosubstituted or disubstituted cyclohexyl or cyclohexenyl, the substituents being independently selected from the group consisting of i-propyl, t-butyl, neo-pentyl, 1,1-dimethylpropyl, 1,1,2-trimethyl-propyl, cyclohexylmethyl or 2-cyclohexyl-2-propyl; or represents decahydronaphthyl which is optionally monosubstituted or disubstituted by methyl, ethyl, methoxy or ethoxy, the substituents being identical or different; or represents in each case optionally monosubstituted or disubstituted phenyl or naphthyl, the substituents being independently selected from the group consisting of fluorine, chlorine, bromine, isopropyl, t-butyl, neo-pentyl, 1,1-dimethylpropyl, 1,1,2-trimethylpropyl, trifluoromethyl, trifluoromethoxy, cyclohexylmethyl, cyclohexyl, phenyl, phenoxy, benzyl, 1-phenylethyl, 2-phenyl-2-propyl, methyl, ethyl, methoxy and ethoxy; or represents 2-thienyl or 3-thienyl which is in each case optionally substituted by chlorine, methyl, i-propyl or t-butyl, $R^2$ represents methyl, $R^3$ represents hydrogen, methyl, ethyl, n- or i-propyl, n-, i- or s-butyl, n-pentyl, n-hexyl, n-octyl, allyl, propargyl, methoxyethyl, methoxypropyl, ethoxyethyl or ethoxypropyl, $R^4$ represents hydrogen or methyl, and Het represents an optionally methyl-substituted heterocyclic ring of the formula

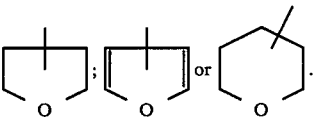

4. A substituted propylamine according to claim 1, wherein such compound is [3-(4-t-butylphenyl)-2-methyl]-N-propyl-N-tetrahydrofuran-2-yl-methylpropylamine of the formula

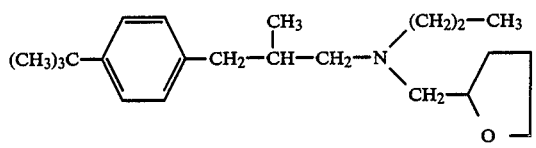

or an acid-addition salt thereof.

5. A substituted propylamine according to claim 1, wherein such compound is [3-(4-t-butylphenyl)-2-methyl]-N-(5-methyl-tetrahydrofuran-2-yl-methyl)-N-methyl-propylamine of the formula

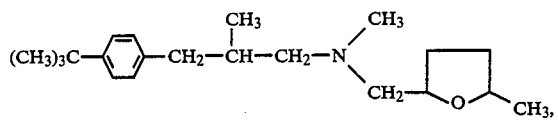

or an acid-addition salt thereof.

6. A substituted propylamine according to claim 1, wherein such compound is [3-(4-t-butylphenyl)-2-methyl]-N-propyl-N-tetrahydropyran-2-yl-methyl-propylamine of the formula

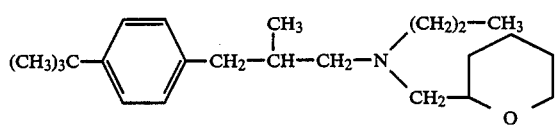

or an acid-addition salt thereof.

7. A substituted propylamine according to claim 1, wherein such compound is [3-(4-t-butylphenyl)-2-methyl]-N-ethyl-N-tetrahydrofuran-2-yl-methyl-propylamine of the formula

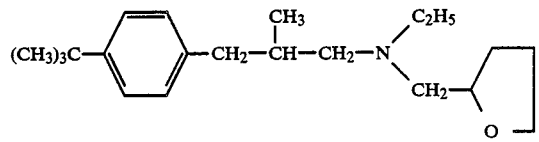

or an acid-addition salt thereof.

8. A pesticidal composition comprising a pesticidally effective amount of a compound or salt according to claim 1 and a diluent.

9. A method of combating pests which comprises applying to such pests or to a pest habitat a pesticidally effective amount of a compound or salt according to claim 1.

10. The method according to claim 9, wherein such compound is
[3-(4-t-butylphenyl)-2-methyl]-N-propyl-N-tetrahydrofuran-2-yl-methyl-propylamine,
[3-(4-t-butylphenyl)-2-methyl]-N-(5-methyl-tetrahydrofuran-2-yl-methyl)-N-methyl-propylamine,
[3-(4-t-butylphenyl)-2-methyl]-N-propyl-N-tetrahydropyran-2-yl-methyl-propylamine or
[3-(4-t-butylphenyl)-2-methyl]-N-ethyl-N-tetrahydrofuran-2-yl-methyl-propylamine,
or an acid-addition salt thereof.

* * * * *